United States Patent

Hudgins et al.

[11] Patent Number: 6,048,319
[45] Date of Patent: Apr. 11, 2000

[54] NON-INVASIVE ACOUSTIC SCREENING DEVICE FOR CORONARY STENOSIS

[75] Inventors: Lonnie H. Hudgins, Aliso Viejo; Premindra A. Chandraratna, Rancho Palos Verdes, both of Calif.

[73] Assignee: Integrated Medical Systems, Inc., Signal Hill, Calif.

[21] Appl. No.: 09/164,618

[22] Filed: Oct. 1, 1998

[51] Int. Cl.$^7$ ..................................................... A61B 7/00
[52] U.S. Cl. .......................................................... 600/528
[58] Field of Search ..................................... 600/508, 528

[56] References Cited

U.S. PATENT DOCUMENTS

| | | | |
|---|---|---|---|
| 3,498,292 | 3/1970 | Jorgensen et al. | 600/528 |
| 3,577,981 | 5/1971 | Kurts | 128/2 R |
| 3,777,740 | 12/1973 | Hokanson | 128/2 V |
| 3,780,725 | 12/1973 | Goldberg | 128/2.05 T |
| 3,878,832 | 4/1975 | Tickner et al. | 600/528 |
| 4,052,977 | 10/1977 | Kay | 128/2 V |
| 4,152,928 | 5/1979 | Roberts | 73/61 R |
| 4,239,047 | 12/1980 | Griggs, III et al. | 128/663 |
| 4,545,387 | 10/1985 | Balique | 128/687 |
| 4,586,514 | 5/1986 | Schlager et al. | 128/773 |
| 4,608,993 | 9/1986 | Albert | 128/663 |
| 4,720,866 | 1/1988 | Elias et al. | 381/67 |
| 4,770,184 | 9/1988 | Green, Jr. et al. | 128/661.08 |
| 4,848,354 | 7/1989 | Angelsen et al. | 128/660.05 |
| 4,905,706 | 3/1990 | Duff et al. | 128/701 |
| 4,922,917 | 5/1990 | Dory | 128/660.01 |
| 5,010,889 | 4/1991 | Bredesen et al. | 128/715 |
| 5,036,837 | 8/1991 | Semmlow et al. | 600/528 |
| 5,119,820 | 6/1992 | Rossman et al. | 128/661.03 |
| 5,162,991 | 11/1992 | Chio | 364/413.03 |
| 5,183,046 | 2/1993 | Beach et al. | 128/661.07 |
| 5,265,613 | 11/1993 | Feldman et al. | 120/661.07 |
| 5,309,917 | 5/1994 | Wang et al. | 128/696 |
| 5,348,015 | 9/1994 | Moehring et al. | 128/661.07 |
| 5,360,005 | 11/1994 | Wilk | 128/653.1 |
| 5,564,424 | 10/1996 | Yao | 128/661.09 |
| 5,582,176 | 12/1996 | Swerling et al. | 128/661.09 |

*Primary Examiner*—William E. Kamm
*Attorney, Agent, or Firm*—Stetina Brunda Garred & Brucker

[57] ABSTRACT

Method and apparatus for detecting coronary stenosis. The apparatus comprises an acoustic sensor and a microcomputer that identifies the standard S1 and S2 heart sounds, heart rate, and determines the diastolic interval of the subject and thereafter estimates the acoustic energy levels within a 2 octave band around approximately 20 Hz during diastole. Based upon such estimation, a diagnosis can be rendered as to the presence and degree of stenosis from the coronary artery.

7 Claims, 1 Drawing Sheet

NON-INVASIVE ACOUSTIC SCREENING DEVICE FOR CORONARY STENOSIS

FIELD OF THE INVENTION

The present invention relates generally to methods and apparatus for the detection of heart disease, and more particularly, to apparatus and methods for rapidly and automatically detecting the presence of coronary stenosis using passive, non-invasive, and inexpensive acoustic technology.

BACKGROUND OF THE INVENTION

As is widely recognized by the medical community, heart disease is the number one contributor to premature death in this country, and coronary stenosis, i.e., the progressive narrowing of the coronary artery caused by a build-up of plaque on the inner arterial wall, is by far the most pervasive form of this disorder. As the coronary artery becomes progressively narrower, the blood supply to the heart muscle is consequently reduced, and thus greatly increases the risk of thrombosis and myocardial infarction in the individual afflicted with such condition.

In this country alone, coronary stenosis kills approximately half (½) a million people every year. Unfortunately, due to the fact that sudden death is one of the most common manifestations of coronary stenosis, a substantial number of those killed by coronary stenosis die before any kind of emergency medical treatment can be administered. In fact, this aspect of heart disease is so prevalent that in the United States alone, the cost of coronary care—the medical treatment of heart problems—substantially exceeds one hundred billion dollars ($100,000,000,000.00) annually.

While numerous attempts have been made to develop methods for detecting the presence of arteriosclerosis before it advances to a critical stage, to date, none have proven successful. In this regard, such methods have suffered from the drawback of not providing reliable results that can be readily interpreted. For example, U.S. Pat. No. 4,905,706, issued to Duff et al, discloses a method and apparatus for the detection of heart disease based upon an analysis of the characteristic sounds of the heart. Such technique is based upon the analysis of a few milliseconds of a phonocardiogram (PCG) occurring between certain identified heart sounds. Specifically, such sounds analyzed involved those which occur after diastolic blood flow begins, and are initiated by the third heart sound S3, and terminating by the fourth heart sound S4, this interval lasting approximately one hundred and thirty-three milliseconds thereafter. Because such interval is so brief and so difficult to detect, the results produced by the techniques disclosed in U.S. Pat. No. 4,905,706 are generally unreliable. Indeed, in order to insure any degree of accuracy, an electrocardiogram (ECG) must necessarily be utilized in performing the procedures disclosed in U.S. Pat. No. 4,905,706, which as a consequence substantially increases the costs of performing such procedures.

Moreover, while other devices and techniques are available for use in monitoring various cardiac parameters, such techniques, which include ultrasonic and electrocardiographic, require complex, expensive equipment. As such, such screening procedures cannot feasibly be conducted on a large scale for the general population.

It would therefore be desirable and advantageous to devise a simple, safe, and non-invasive method and apparatus for identifying coronary stenosis. Ideally, such device would be usable by technicians and other non-medical personnel in screening large groups of people, without the need for special medical facilities and the like. There is further need in the art for such a method and apparatus for the early detection of coronary stenosis that utilizes conventional diagnostic equipment and can be utilized at substantially reduced cost relative to conventional techniques in use for monitoring various cardiac parameters. There is still further a need for methods and apparatus for the early detection of coronary stenosis that is capable of producing continuously reliable results, irrespective of the patient population with which the same are utilized.

SUMMARY OF THE INVENTION

The present invention specifically addresses and alleviates the aforementioned deficiencies in the art. Specifically, the present invention is directed to devices and methods to provide early detection of coronary stenosis based upon readily discernable sounds produced by the heart. With respect to the preferred embodiment of the device of the present invention, such device preferably combines an acoustic sensor and a microcomputer. The sensor is specifically designed and configured to detect acoustic energy emitted from the heart when held in close contact with a subject's left chest. The acoustic impedance of the sensor is matched to human tissue, and is capable of resolving detailed cardiac sounds. Specifically, the heart sounds sought to be identified and analyzed for purposes of the present invention emanate during the interval ending with first heart sound, S1, which is caused by the closure of the atrioticular valve (the tri-cuspid valve and the bi-cuspid or mitral valve) and the contraction of the ventricles, and beginning with a second heart sound, S2, caused by the closing of the aortic and pulmonary valves. The microcomputer processes the signal generated by the sound, via a signal processing algorithm, to passively determine certain fluid-mechanical characteristics of the blood flow through the coronary artery. Determinations are made with respect to heart rate and systolic interval from which an estimation is made as to the acoustic energy levels during diastole. Such estimation provides a basis for indicating the health status of the coronary artery.

It is therefore an object of the present invention to provide a method and apparatus for detecting cardiovascular disease, in particular, coronary stenosis.

Another object of the present invention is to provide a method and apparatus which does not require invasion of the body by instrument or acoustic waves or electromagnetic radiation for purposes of rendering a diagnosis.

Another object of the present invention is to provide a health screening device for coronary stenosis that may be easily and readily utilized by non-medical personnel that further incorporates the use of conventional equipment, is therefore less expensive than prior art methods and techniques.

BRIEF DESCRIPTION OF THE DRAWINGS

The novel features and characteristics of the invention are set forth in the appended claims. The invention itself, however, as well as a preferred mode of use, further objects and advantages thereof, will best be understood by reference to the following detailed description of illustrative embodiments when read in conjunction with accompanying drawing, wherein:

DETAILED DESCRIPTION OF THE PREFERRED EMBODIMENT

Figure 1:
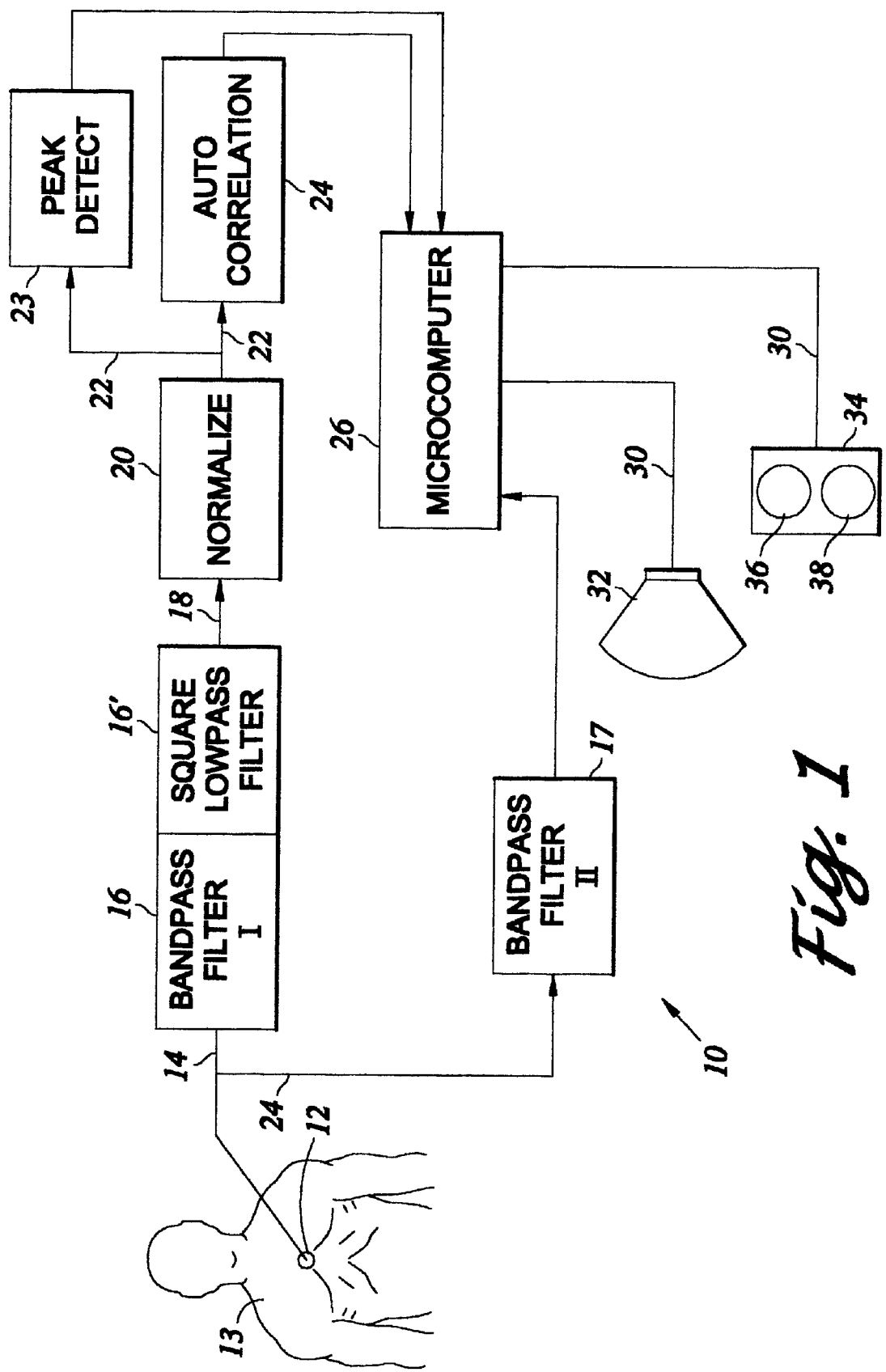
FIG. 1 is a block diagram showing the general components of the acoustic health-screening device for coronary stenosis according to the preferred embodiment of the present invention.

The detailed description set forth below in connection with the appended drawing is intended merely as a description of the presently preferred embodiment of the invention, and is not intended to represent the only form in which the present invention may be constructed or utilized. The description sets forth the functions and sequence of steps for construction and implementation of the invention in connection with the illustrated embodiment. It is to be understood, however, that the same or equivalent functions and sequences may be accomplished by different embodiments that are also intended to be encompassed within the spirit and scope of the invention.

Referring now to the drawing, i.e., FIG. 1, there is shown a block diagram showing the general components of the device 10 of the present invention. Such device is specifically designed and configured to quickly, easily and inexpensively detect cardiovascular disease, and in particular, coronary stenosis.

As is well known to those skilled in the art, by virtue of its pumping action, the heart generates acoustical activity that, to date, has had limited utility as diagnostic indicators when viewed by an experienced cardiologist. By way of background, it is well known that a first heart sound S1 commences about the same time the heart beat commences, and continues during the time the stimulus is generated which triggers the ventricle contraction which produces the actual cardiac pumping action. More specifically, such sound is caused by the closure of the atrioventricular valves (the tricuspid valve and the bicuspid or mitral valve) and the contraction of the ventricles.

After a brief interval, a second rapid heart sound S2 appears, caused by the closing of the aortic and pulmonary valves. Diastolic blood flow begins after the second heart sound, sometimes resulting in a discernable third heart sound S3. It is presently believed that the third heart sound, when present, is caused by the oscillation of blood back and forth between the walls of the ventricles initiated by inrushing blood from the atria. A fourth heart sound S4, also known as the atrial heart sound, is more rare, and can occur when the atria contract, which initiates vibrations in the ventricles similar to the third heart sound.

Thus, the four heart sounds result from valve closure (S1 and S2), oscillation of blood between the walls of the ventricle (S3) or contraction of the atria (S4). With respect to the present invention, the device 10 is specifically designed to determine the sound energy level emanating from the coronary artery, during the interval between sounds S2 and S1. Advantageously, because the duration of the interval between the S2 and S1 sounds can last approximately one (1) second, there is thus provided a relatively long interval of acoustical activity that may be evaluated and processed to thus generate more reliable results in detecting coronary artery disease than prior art methods, as well as the extent of the progression thereof, if applicable. In this regard, unlike prior art methods which utilize only a few milliseconds of acoustical activity data, such interval enables the techniques of the present invention to be easily and readily practiced insofar as the degree of precision necessary to capture the precise heart sounds indicative of coronary heart disease are substantially lessened. As such, the techniques of the present invention may be practiced inexpensively and on a much larger scale than prior art methods and techniques.

In regard to the present invention, screening for coronary artery disease is based upon the well established principle that excessive sound levels during the diastole interval are typically indicative of coronary stenosis. To make such determination, the system 10 employs an acoustic sensor or microphone 12 which is placed upon the chest 13 of the subject. Such acoustic sensors or microphones 12 are known in the art and are designed to pick-up internal acoustical activity. One preferred sensor 12 comprises a modified, hand-held surgical table integral heart-rate sensor. Initially, the acoustic impedance of the microphone 12 is matched to human tissue, and is thus designed to resolve detailed cardiac sounds. The output 14 from the microphone 12 is passed, through a bandpass filter I 16 and square/low past filter 16', which preferably limits recordation only to those heart sounds whose frequency content lies between about 50–500 Hz. Accordingly, the bandpass filter I 16 and square/low pass filter 16' pass only frequencies within this range, removing the large amount of energy contained in the major heart sounds at frequencies below 50 Hz, and attenuating any noise having a frequency above 500 Hz. The resultant signal 18 is thereafter normalized 20 for unit variance. Using peak-detection and thresholding, via techniques well known to those skilled in the art, various heart sounds are identified from the normalized signal 22, and more particularly the heart sounds S1, S2, and when applicable S3 and S4, as identified above.

From the normalized signal 22, an additional autocorrelation function 24 is completed. As is well known to those skilled in the art, autocorrelation measures the degree of repeatability of various signal characteristics, and is used here to determine the heart beat interval, as well as the typical period of time between heart sounds S1 and S2, these being determined by the signal generated from the acoustic sensor via well-known techniques in the art.

Thereafter, from the signal generated from peak detection and thresholding 23, a microcomputer 26 determines the aforementioned interval between S1 and S2 sounds. As may be determined graphically, such interval may be determined as the largest peak between the central peak and one-half of the heart beat interval in the aforementioned auto correlation function. In this regard, it will be recognized that a signal generated from the acoustic sensor will necessarily indicate those sounds generated between the range of 50 to 500 Hz, as well as provide an indication as to the strength of such signal. As such sounds are generated over time, there will thus be generated a pattern, systematic, rhythmic sounds that are generated that, once normalized, will provide a plurality of peaks, with the S1 and S2 intervals being the largest peak between the central peak and the one-half the heart beat interval in the auto correlation function 22 discussed above.

The microcomputer 26 thereafter estimates the acoustic energy levels during diastole based upon analysis of the signal generated by the acoustic signal over a plurality of heart beats. Specifically, once the heart beat interval and S1 and S2 interval are identified, the clarification is made with respect to heart sounds being discernible as either S1 or S2. Having made such determination of the sounds S1 and S2, the diastolic interval, namely the lapse of time beginning with S2 and ending with S1, there may subsequently be determined using classical Fourier methods or any other suitable method or circuitry the energy within such S2-S1 interval, and in particular, a two-octave band around 20 Hz which is measured according to well-recognized principles, and is depicted in FIG. 1 as bandpass II 17.

The diastolic energy, as indicated from the microprocessor's analysis of the signal generated by the acoustic sensor, thus provides an indication as to whether the rating is indicative of sound patterns consistent with coronary stenosis as compared to known baseline parameters. Additionally, such diastolic sound signal 30 can be modified and combined with the heart valve sounds and thereafter reproduced on a speaker 32 to thus provide an indication as to the relative strength of the sounds to one another. As discussed above, excessive sound levels during diastole are indicative of coronary stenosis and, as such, such sound levels, which are otherwise absent in healthy individuals, will thus provide a clearly audible indication relative to the S1 and S2 heart sounds so as to provide a clearly audible indication that a given subject is afflicted with coronary stenosis.

Advantageously, by providing such acoustical indication, as opposed to complex graphical data, the device of the present invention may be utilized by relatively untrained personnel to thus screen large numbers of individuals in a rapid amount of time. In this regard, the technician need only listen for certain sound patterns indicative of coronary stenosis and, to the extent the same can be readily identified by applying the microphone to the chest of the individual after the signal generated thereby has been normalized, there would appear to be no need for the interpretation of complex statistical data.

In an alternative, more simplified embodiment, the diastolic sound signal is analyzed by the microcomputer 26 and is compared to known baseline parameters. The microcomputer 26 thereafter provides an output signal 30 to a simple visual indicator 34, such as a green-red LED. To the extent coronary artery disease is present, the signal 30 will cause the visual indicator 34 to produce a visual signal, such as a red light 36 to illuminate, to thus provide a signal that the patient is afflicted with such condition. To the extent that coronary artery disease is not present, the signal 30 will cause the green light 38 to illuminate to thus indicate the absence of coronary artery disease.

Although the invention has been described herein with specific reference to a presently preferred embodiment thereof, it will be appreciated by those skilled in the art that various additions, modifications, deletions and alterations may be made to such preferred embodiment without departing from the spirit and scope of the invention. Accordingly, it is intended that all reasonably foreseeable additions, modifications, deletions and alterations be included within the scope of the invention as defined in the following claims.

What is claimed is:

1. A system for detecting coronary artery disease from an acoustical signal generated from a heartbeat of a human subject, said apparatus comprising:
    a) a microphone for converting the acoustical signal generated from said heartbeat into an electrical signal;
    b) a computer for processing said electrical signal to identify a first sound corresponding to the closure of the atrioventricular valves and the contraction of the ventricles, and a second sound corresponding to the closure of the aortic and pulmonary valves, and thereafter determining the interval between said first and second cardiac sounds; and
    c) wherein said computer is further operative to determine the heart rate of said human and compare the same to said interval between said first and second cardiac sounds to thus quantify the diastolic energy emanating from the coronary artery during diastole and thereafter comparing said diastolic energy to baseline parameters such that the presence and degree of coronary artery disease may be detected.

2. The system of claim 1 further comprising:
    d) a speaker coupled to said computer, said speaker being designed to provide an acoustical indication of the presence and degree of coronary artery disease by reproducing sounds from signals generated from said computer indicative of coronary artery disease.

3. The system of claim 1 further comprising:
    d) a visual indicator coupled to said computer, said visual indicator being designed and configured to provide a first signal operative to indicate the presence of coronary artery disease, and a second signal operative to indicate the absence of coronary artery disease.

4. The apparatus of claim 1 wherein said microphone of said system comprises a phonocardiogram microphone for detecting cardiac acoustical activity consisting of a plurality of heart beats.

5. A method of detecting coronary artery disease in a human subject comprising the steps of:
    a) detecting an acoustical signal generated from a heartbeat of said subject and converting said acoustical signal into an electrical signal;
    b) processing said electrical signal generated in step a) to identify a first heart sound corresponding to the closure of the atrioventricular valves and the contraction of the ventricles, and a second heart sound corresponding to the closure of the aortic and pulmonary valves during said heartbeat, and the interval between said first and second heart sound;
    c) determining the heart rate of said individual;
    d) comparing the heart rate interval and the interval between said second and first heart sounds and estimating the sound energy level emanating from the coronary artery during said interval between said second and first heart sounds; and
    e) comparing said energy level determined in step d) to a baseline energy level and identifying whether said energy level determined in step d) is indicative of coronary artery disease.

6. The method of claim 5 wherein in step e), the determination as to whether the human is afflicted with coronary artery disease is indicated by acoustically modifying the diastolic heart sounds between said second and first heart sounds, and presenting said sounds to a human operator via a speaker.

7. The method of claim 5 wherein in step e), the determination as to whether the human is afflicted with coronary artery disease is indicated by providing a visual signal.

* * * * *